United States Patent
Gon et al.

(10) Patent No.: US 11,993,744 B2
(45) Date of Patent: May 28, 2024

(54) SOLID PARAFFIN INHIBITOR AND CORROSION INHIBITOR COMPOSITIONS

(71) Applicant: ChampionX LLC, Sugar Land, TX (US)

(72) Inventors: Saugata Gon, Rosenberg, TX (US); Jeremy Moloney, Katy, TX (US); Boyd Anthony Laurent, Pearland, TX (US); Andrew Robert Neilson, Richmond, TX (US)

(73) Assignee: ChampionX USA Inc., Sugarland, TX (US)

( * ) Notice: Subject to any disclaimer, the term of this patent is extended or adjusted under 35 U.S.C. 154(b) by 0 days.

(21) Appl. No.: 18/299,214

(22) Filed: Apr. 12, 2023

(65) Prior Publication Data

US 2023/0323188 A1 Oct. 12, 2023

Related U.S. Application Data

(60) Provisional application No. 63/362,845, filed on Apr. 12, 2022.

(51) Int. Cl.
| | |
|---|---|
| *C09K 8/524* | (2006.01) |
| *C07C 211/63* | (2006.01) |
| *C07D 233/02* | (2006.01) |
| *C07D 233/10* | (2006.01) |
| *C09K 8/54* | (2006.01) |

(52) U.S. Cl.
CPC ............ *C09K 8/524* (2013.01); *C07C 211/63* (2013.01); *C07D 233/02* (2013.01); *C07D 233/10* (2013.01); *C09K 8/54* (2013.01); *C09K 2208/32* (2013.01)

(58) Field of Classification Search
None
See application file for complete search history.

(56) References Cited

U.S. PATENT DOCUMENTS

| | | | |
|---|---|---|---|
| 2,468,163 A | 4/1949 | Blair, Jr. et al. | |
| 4,986,353 A | 1/1991 | Clark et al. | |
| 5,858,927 A | 1/1999 | Poelker et al. | |
| 6,100,221 A | 8/2000 | Poelker et al. | |
| 7,057,050 B2 | 6/2006 | Meyer | |
| 7,475,730 B2 | 1/2009 | Brown et al. | |
| 7,598,209 B2 | 10/2009 | Kaufman et al. | |
| 7,857,871 B2 | 12/2010 | Martin et al. | |
| 9,010,430 B2 | 4/2015 | Darby et al. | |
| 9,303,236 B2 | 4/2016 | Bennett et al. | |
| 9,410,073 B2 | 8/2016 | Webber et al. | |
| 9,976,070 B2 | 5/2018 | Gupta et al. | |
| 10,000,641 B2 | 6/2018 | Miles et al. | |
| 10,113,101 B2 | 10/2018 | Soriano, Jr. et al. | |
| 10,487,278 B2 | 11/2019 | Solomon | |
| 10,717,918 B2 * | 7/2020 | Fouchard | E21B 37/06 |
| 10,876,033 B2 | 12/2020 | Oskarsson et al. | |
| 2004/0110877 A1 * | 6/2004 | Becker | C09K 8/54 |
| | | | 524/114 |
| 2004/0200996 A1 | 10/2004 | Meyer | |
| 2006/0183843 A1 | 8/2006 | Baloche et al. | |
| 2009/0114879 A1 * | 5/2009 | Hellsten | C09K 8/524 |
| | | | 252/182.29 |
| 2014/0190692 A1 * | 7/2014 | Hibbeler | E21B 21/062 |
| | | | 166/308.4 |
| 2018/0148632 A1 | 5/2018 | Bennett et al. | |
| 2018/0340114 A1 * | 11/2018 | Fouchard | C09K 8/54 |
| 2020/0017750 A1 | 1/2020 | Mahmoudkhani et al. | |
| 2020/0157417 A1 | 5/2020 | Bhaduri et al. | |
| 2020/0299560 A1 | 9/2020 | Bhaduri et al. | |
| 2020/0339871 A1 | 10/2020 | Obot et al. | |

FOREIGN PATENT DOCUMENTS

| | | |
|---|---|---|
| CN | 1966774 A | 5/2007 |
| CN | 108165247 A | 6/2018 |
| WO | 2020/046670 A1 | 3/2020 |
| WO | 2021/018467 A1 | 2/2021 |
| WO | 2021/041844 A1 | 3/2021 |

OTHER PUBLICATIONS

Xu, Jun et al., How comb-type poly(maleic acid alkylamide-co-α-olefin) assemble in waxy oils and improve flowing ability, Asia-Pacific Journal of Chemical Engineering (2009) 4, pp. 551-556.

Wei, Bing, Recent advances on mitigating wax problem using polymeric wax crystal modifier, J. Petrol Explor Prod Technol (Dec. 4, 2014), 11 pages.

Zarrouki, A. et al., Free Radical Copolymerization of Ethylene with Vinyl Acetate under Mild Conditions, Macromolecules (2017) 50, pp. 3516-3523.

Shipp, Devon A. et al., Synthesis of Acrylate and Methacrylate Block Copolymers Using Atom Transfer Radical Polymerization, Macromolecules (1998) 31, pp. 8005-8008.

International Search Report and Written Opinion dated Aug. 3, 2023 relating to PCT Patent Application No. PCT/US2023/018284, 14 pages.

* cited by examiner

*Primary Examiner* — John J Figueroa
(74) *Attorney, Agent, or Firm* — Stinson LLP

(57) ABSTRACT

The present disclosure describes solid compositions comprising a paraffin inhibitor and a corrosion inhibitor. The paraffin inhibitors include polymers having various repeat units containing one or more ester moieties. The corrosion inhibitors can be imidazoline compounds, quaternary ammonium compounds, or a combination thereof. These solid compositions can be used to treat subterranean hydrocarbon-containing reservoir and can inhibit or reduce paraffin deposition in the reservoir and/or inhibit or reduce corrosion in a piece of equipment in contact with the reservoir.

20 Claims, No Drawings

SOLID PARAFFIN INHIBITOR AND CORROSION INHIBITOR COMPOSITIONS

FIELD

The present disclosure describes solid compositions comprising a paraffin inhibitor and a corrosion inhibitor. The paraffin inhibitors include polymers having various repeat units containing one or more ester moieties. The corrosion inhibitors can be imidazoline compounds, quaternary ammonium compounds, or a combination thereof. These solid compositions can be used to treat subterranean hydrocarbon-containing reservoir and can inhibit or reduce paraffin deposition in the reservoir and/or inhibit or reduce corrosion in a piece of equipment in contact with the reservoir.

BACKGROUND

Oilfield fluids are complex mixtures of aliphatic hydrocarbons, aromatics, compound containing heteroatoms, anionic and cationic salts, acids, water, gas, and myriad other components. With this complex mixture comes problems with deposition of various components in unwanted portions of the extraction process. For example, deposition of scale, salts, paraffins, asphaltene, bacteria, and the like can occur during the extraction process.

This deposition process of various components can lead to restriction or plugging in production piping or the flow path of the mixture in the reservoir. Various treatments to remedy this plugging or restriction of flow paths has been performed including both mechanical and chemical treatments with varying success.

One treatment method is to provide solid chemical additives to oil wells that dissolve in the reservoir fluid and affect the deposition and flow of the reservoir fluids. Some solid chemical additives are suitable only for particular types of wells or require additional equipment to flush the solid chemical into the correct position in the reservoir.

Thus, a need exists for effective and efficient solid compositions for treatment of oilfield fluids and for a more effective and efficient method for treating oilfield fluids with the solid treatment compositions.

SUMMARY

This disclosure describes a solid composition comprising a paraffin inhibitor and a corrosion inhibitor. The paraffin inhibitor comprises a polymer having the structure corresponding to Formulae 1, 2, or 3:

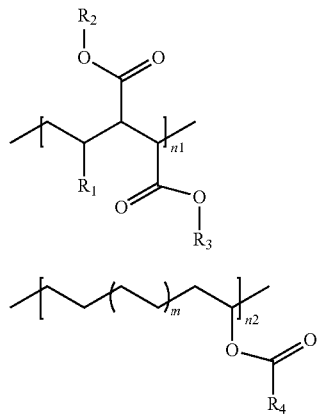

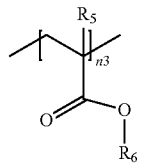

wherein $R_1$ and $R_5$ are independently hydrogen, alkyl, or alkaryl; $R_2$ and $R_3$ are independently selected from $C_{10}$ to $C_{30}$ alkyl or $C_{10}$ to $C_{30}$ alkenyl; $R_4$ and $R_6$ are independently selected from alkyl or alkenyl; n1 is an integer from 10 to 200 (or weight average molecular weight from about 1000 Daltons to about 100,000 Daltons); n2 is an integer from 30 to 50,000 (or weight average molecular weight from about 1000 Daltons to about 100,000,000 Daltons); n3 is an integer from 50 to 2000 (or a weight average molecular weight from about 10,000 to 300,000 Daltons); m is an integer from 1 to 12. The corrosion inhibitor comprises (i) an imidazoline compound having the structure of Formula 4:

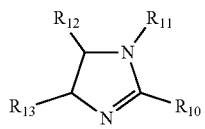

wherein $R_{10}$ is $C_1$ to $C_{20}$ alkyl or $C_1$ to $C_{20}$ alkenyl; $R_{12}$ and $R_{13}$ are independently hydrogen or $C_1$ to $C_6$ alkyl; and $R_{11}$ is $C_1$ to $C_6$ alkyl substituted with $-N(R_{21})(R_{22})$ or $-C(O)OR_{24}$, $R_{21}$ is hydrogen or $-(CO)R_{23}$; $R_{22}$ is $-(CO)R_{23}$; $R_{23}$ is $C_{10}$ to $C_{20}$ alkyl or $C_{10}$ to $C_{20}$ alkenyl; and $R_{24}$ is hydrogen or $C_1$ to $C_6$ alkyl; or a tautomer thereof; (ii) an imidazole compound having the structure of Formula 5:

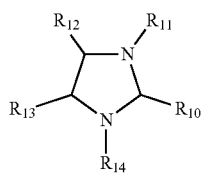

wherein $R_{10}$ is $C_1$ to $C_{20}$ alkyl or $C_1$ to $C_{20}$ alkenyl; $R_{12}$ and $R_{13}$ are independently hydrogen or $C_1$ to $C_6$ alkyl; and $R_{11}$ and $R_{14}$ are independently $C_1$-$C_6$ alkyl substituted with $-N(R_{21})(R_{22})$ or $-C(O)OR_{24}$; $R_{21}$ is hydrogen, $-(CO)R_{23}$, or $C_1$-$C_6$ alkyl substituted with $-C(O)OR_{24}$; $R_{22}$ is $-(CO)R_{23}$ or $C_1$-$C_6$ alkyl substituted with $-C(O)OR_{24}$; $R_{23}$ is $C_{10}$ to $C_{20}$ alkyl or $C_{10}$ to $C_{20}$ alkenyl; and $R_{24}$ is hydrogen or $C_1$ to $C_6$ alkyl; or a tautomer thereof; (iii) a quaternary ammonium compound having the structure of Formula 6

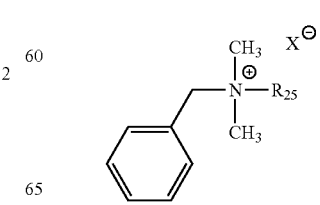

wherein $R_{25}$ is $C_6$ to $C_{20}$ alkyl or $C_6$ to $C_{20}$ alkyl wherein one or more —$CH_2$— is replaced with —O— or -(iv) a combination thereof.

The solid compositions described herein can have the solid composition be in the form of a pellet.

The solid compositions disclosed herein can have the paraffin inhibitor comprise the polymer having the structure of Formula 1.

When the paraffin inhibitor comprises the polymer having the structure of Formula 1, $R_1$ is $C_{10}$ to $C_{40}$ alkyl; $R_1$ is $C_{12}$ to $C_{36}$ alkyl; $R_1$ is $C_{10}$ to $C_{16}$ alkyl; $R_1$ is $C_{20}$ to $C_{24}$ alkyl; or $R_1$ is $C_{24}$ to $C_{36}$ alkyl.

When the paraffin inhibitor comprises the polymer having the structure of Formula 1, $R_2$ and $R_3$ are independently $C_{10}$ to $C_{30}$ alkyl; $R_2$ and $R_3$ are independently $C_{16}$ to $C_{28}$ alkyl; $R_2$ and $R_3$ are independently $C_1$ to $C_{22}$ alkyl; or $R_2$ and $R_3$ are independently $C_{20}$ to $C_{28}$ alkyl.

Additionally, the solid compositions can have the paraffin inhibitor have the structure of Formula 2 and $R_4$ is $C_{12}$ to $C_{30}$ alkyl.

Further, the solid compositions described herein can have paraffin inhibitor have the structure of Formula 3; and have $R_5$ be hydrogen or methyl; and $R_6$ be $C_{12}$ to $C_{30}$ alkyl.

The solid compositions described herein can have a polymer of Formula 1 have a weight average molecular weight from about 1000 Daltons to about 30,000 Daltons.

Additionally, the solid compositions described herein can have the corrosion inhibitor comprise the imidazoline compound of Formula 4.

When the corrosion inhibitor comprises the imidazoline compound of Formula 4, $R_{10}$ is a $C_{10}$ to $C_{20}$ alkyl or a $C_{10}$ to $C_{20}$ alkenyl; or $R_{10}$ is $C_{16}$ to $C_{18}$ alkyl or $C_{16}$ to $C_{20}$ alkenyl.

When the corrosion inhibitor comprises the imidazoline compound of Formula 4, $R_{12}$ and $R_{13}$ are hydrogen.

When the corrosion inhibitor comprises the imidazoline compound of Formula 4, $R_{11}$ is $C_1$ to $C_6$ alkyl substituted with —$N(R_{21})(R_{22})$; $R_{21}$ is hydrogen; $R_{22}$ is —$(CO)R_{23}$; and $R_{23}$ is $C_{10}$ to $C_{20}$ alkyl or $C_{10}$ to $C_{20}$ alkenyl.

Further, the solid composition disclosed herein can have the corrosion inhibitor comprise the imidazoline compound of Formula 5.

When the corrosion inhibitor comprises the imidazoline compound of Formula 5, $R_{10}$ is a $C_{10}$ to $C_{20}$ alkyl or a $C_{10}$ to $C_{20}$ alkenyl; or $R_{10}$ is $C_{16}$ to $C_{18}$ alkyl or $C_{16}$ to $C_{20}$ alkenyl.

When the corrosion inhibitor comprises the imidazoline compound of Formula 5, $R_{12}$ and $R_{13}$ are hydrogen.

When the corrosion inhibitor comprises the imidazoline compound of Formula 5, $R_{11}$ is $C_1$ to $C_6$ alkyl substituted with —$N(R_{21})(R_{22})$; $R_{21}$ is hydrogen; $R_{22}$ is —$(CO)R_{23}$; and $R_{23}$ is $C_{10}$ to $C_{20}$ alkyl or $C_{10}$ to $C_{20}$ alkenyl.

When the corrosion inhibitor comprises the imidazoline compound of Formula 5, $R_{14}$ is $C_1$-$C_6$ alkyl substituted with —$C(O)OR_{24}$; and $R_{24}$ is hydrogen or $C_1$ to $C_3$ alkyl.

The solid compositions described herein can also have the corrosion inhibitor comprise the quaternary ammonium compound having the structure of Formula 6, wherein $R_{25}$ is $C_8$ to $C_{16}$ alkyl.

Preferably, the solid compositions described herein have the paraffin inhibitor comprise the polymer of Formula 1 and the corrosion inhibitor comprise the compound of Formula 4 and the compound of Formula 5, wherein a weight ratio of the paraffin inhibitor to the corrosion inhibitor is from about 1:5 to about 5:1. Preferably, the weight ratio of the paraffin inhibitor to the corrosion inhibitor is from about 1:2 to about 2:1; or the ratio of the paraffin inhibitor to the corrosion inhibitor is about 1:1.

Also disclosed are method for treating a subterranean hydrocarbon-containing reservoir comprising contacting the hydrocarbon with a solid composition described herein.

For the methods of treating a subterranean hydrocarbon-containing reservoir, the solid composition can inhibit or reduce paraffin deposition in the reservoir.

Also, in the methods of treating a subterranean hydrocarbon-containing reservoir, the solid composition can inhibit or reduce corrosion in a piece of equipment in contact with the reservoir.

Other objects and features will be in part apparent and in part pointed out hereinafter.

DESCRIPTION OF THE PREFERRED EMBODIMENTS

The present disclosure describes a class of solid paraffin inhibitor compositions which exhibit corrosion inhibition properties. Using solid treatment compositions has numerous benefits over typical liquid oilfield chemicals including a lack of freeze point or flash point limitations and ease of injection in certain type of applications. The solid compositions described herein have these benefits and also can inhibit paraffin deposition in the reservoir and inhibit corrosion of the production equipment. Additionally, the methods of treatment of the reservoir using these solid compositions provide simplified logistics and reduced chemical handling.

This disclosure describes a solid composition comprising a paraffin inhibitor and a corrosion inhibitor. The paraffin inhibitor comprises a polymer having the structure corresponding to Formulae 1, 2, or 3:

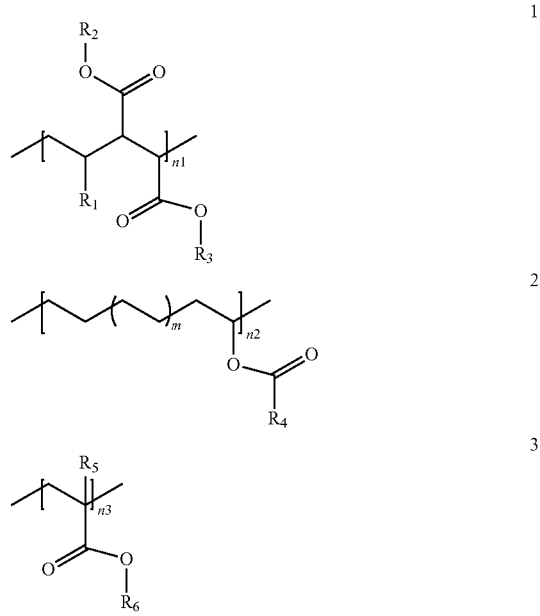

wherein $R_1$ and $R_5$ are independently hydrogen, alkyl, or alkaryl; $R_2$ and $R_3$ are independently selected from $C_{10}$ to $C_{30}$ alkyl or $C_{10}$ to $C_{30}$ alkenyl; $R_4$ and $R_6$ are independently selected from alkyl or alkenyl; n1 is an integer from 10 to 200 (or weight average molecular weight from about 1000

Daltons to about 100,000 Daltons); n2 is an integer from 30 to 50,000 (or weight average molecular weight from about 1000 Daltons to about 100,000,000 Daltons); n3 is an integer from 50 to 2000 (or a weight average molecular weight from about 10,000 to 300,000 Daltons); m is an integer from 1 to 12. The corrosion inhibitor comprises (i) an imidazoline compound having the structure of Formula 4:

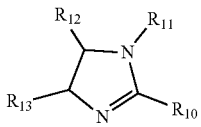

4 wherein $R_{10}$ is $C_1$ to $C_{20}$ alkyl or $C_1$ to $C_{20}$ alkenyl; $R_{12}$ and $R_{13}$ are independently hydrogen or $C_1$ to $C_6$ alkyl; and $R_{11}$ is $C_1$ to $C_6$ alkyl substituted with —$N(R_{21})(R_{22})$ or —$C(O)OR_{24}$, $R_{21}$ is hydrogen or —$(CO)R_{23}$; $R_{22}$ is —$(CO)R_{23}$; $R_{23}$ is $C_{10}$ to $C_{20}$ alkyl or $C_{10}$ to $C_{20}$ alkenyl; and $R_{24}$ is hydrogen or $C_1$ to $C_6$ alkyl; or a tautomer thereof; (ii) an imidazole compound having the structure of Formula 5:

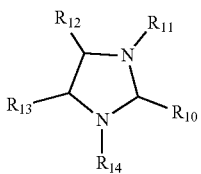

5 wherein $R_{10}$ is $C_1$ to $C_{20}$ alkyl or $C_1$ to $C_{20}$ alkenyl; $R_{12}$ and $R_{13}$ are independently hydrogen or $C_1$ to $C_6$ alkyl; and $R_{11}$ and $R_{14}$ are independently $C_1$-$C_6$ alkyl substituted with —$N(R_{21})(R_{22})$ or —$C(O)OR_{24}$; $R_{21}$ is hydrogen, —$(CO)R_{23}$, or $C_1$-$C_6$ alkyl substituted with —$C(O)OR_{24}$; $R_{22}$ is —$(CO)R_{23}$ or $C_1$-$C_6$ alkyl substituted with —$C(O)OR_{24}$; $R_{23}$ is $C_{10}$ to $C_{20}$ alkyl or $C_{10}$ to $C_{20}$ alkenyl; and $R_{24}$ is hydrogen or $C_1$ to $C_6$ alkyl; or a tautomer thereof; (iii) a quaternary ammonium compound having the structure of Formula 6

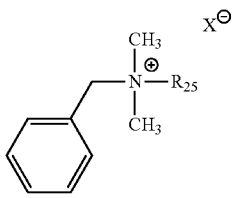

6 wherein $R_{25}$ is $C_6$ to $C_{20}$ alkyl or $C_6$ to $C_{20}$ alkyl wherein one or more —$CH_2$— is replaced with —$O$— or -(iv) a combination thereof.

The solid compositions described herein can have the solid composition be in the form of a pellet.

The solid compositions disclosed herein can have the paraffin inhibitor comprise the polymer having the structure of Formula 1:

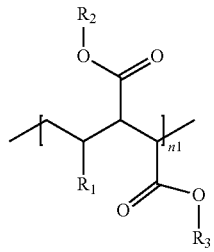

1 wherein $R_1$ is hydrogen, alkyl, or alkaryl; $R_2$ and $R_3$ are independently selected from $C_{10}$ to $C_{30}$ alkyl or $C_{10}$ to $C_{30}$ alkenyl.

When the paraffin inhibitor comprises the polymer having the structure of Formula 1, $R_1$ is $C_{10}$ to $C_{40}$ alkyl; $R_1$ is $C_{12}$ to $C_{36}$ alkyl; $R_1$ is $C_{10}$ to $C_{16}$ alkyl; $R_1$ is $C_{20}$ to $C_{24}$ alkyl; or $R_1$ is $C_{24}$ to $C_{36}$ alkyl.

When the paraffin inhibitor comprises the polymer having the structure of Formula 1, $R_2$ and $R_3$ are independently $C_{10}$ to $C_{30}$ alkyl; $R_2$ and $R_3$ are independently $C_{16}$ to $C_{25}$ alkyl; $R_2$ and $R_3$ are independently $C_1$ to $C_{22}$ alkyl; or $R_2$ and $R_3$ are independently $C_{20}$ to $C_{28}$ alkyl.

When the paraffin inhibitor comprises the polymer having the structure of Formula 1, $R_1$ is $C_{10}$ to $C_{40}$ alkyl; and $R_2$ and $R_3$ are independently $C_{10}$ to $C_{30}$ alkyl.

When the paraffin inhibitor comprises the polymer having the structure of Formula 1, $R_1$ is $C_{10}$ to $C_{16}$ alkyl; and $R_2$ and $R_3$ are independently $C_{10}$ to $C_{30}$ alkyl.

When the paraffin inhibitor comprises the polymer having the structure of Formula 1, $R_1$ is $C_{20}$ to $C_{24}$ alkyl; and $R_2$ and $R_3$ are independently $C_{10}$ to $C_{30}$ alkyl.

When the paraffin inhibitor comprises the polymer having the structure of Formula 1, $R_1$ is $C_{24}$ to $C_{36}$ alkyl; and $R_2$ and $R_3$ are independently $C_{10}$ to $C_{30}$ alkyl.

When the paraffin inhibitor comprises the polymer having the structure of Formula 1, $R_1$ is $C_{10}$ to $C_{40}$ alkyl; and $R_2$ and $R_3$ are independently $C_{18}$ to $C_{22}$ alkyl.

When the paraffin inhibitor comprises the polymer having the structure of Formula 1, $R_1$ is $C_{10}$ to $C_{16}$ alkyl; and $R_2$ and $R_3$ are independently $C_{18}$ to $C_{22}$ alkyl.

When the paraffin inhibitor comprises the polymer having the structure of Formula 1, $R_1$ is $C_{20}$ to $C_{24}$ alkyl; and $R_2$ and $R_3$ are independently $C_1$ to $C_{22}$ alkyl.

When the paraffin inhibitor comprises the polymer having the structure of Formula 1, $R_1$ is $C_{24}$ to $C_{36}$ alkyl; and $R_2$ and $R_3$ are independently $C_{18}$ to $C_{22}$ alkyl.

When the paraffin inhibitor comprises the polymer having the structure of Formula 1, $R_1$ is $C_{10}$ to $C_{40}$ alkyl; and $R_2$ and $R_3$ are independently $C_{20}$ to $C_{28}$ alkyl.

When the paraffin inhibitor comprises the polymer having the structure of Formula 1, $R_1$ is $C_{10}$ to $C_{16}$ alkyl; and $R_2$ and $R_3$ are independently $C_{20}$ to $C_{28}$ alkyl.

When the paraffin inhibitor comprises the polymer having the structure of Formula 1, $R_1$ is $C_{20}$ to $C_{24}$ alkyl; and $R_2$ and $R_3$ are independently $C_{20}$ to $C_{28}$ alkyl.

When the paraffin inhibitor comprises the polymer having the structure of Formula 1, $R_1$ is $C_{24}$ to $C_{36}$ alkyl; and $R_2$ and $R_3$ are independently $C_{20}$ to $C_{28}$ alkyl.

The solid compositions described herein can have a polymer of Formula 1 have a weight average molecular weight from about 1000 Daltons to about 100,000 Daltons; from about 2000 Daltons to about 100,000 Daltons; from about 1000 Daltons to about 80,000 Daltons; from about 2000 Daltons to about 80,000 Daltons; from about 1000

Daltons to about 60,000 Daltons; from about 2000 Daltons to about 60,000 Daltons; from about 1000 Daltons to about 50,000 Daltons; from about 2000 Daltons to about 50,000 Daltons; from about 1000 Daltons to about 40,000 Daltons; or from about 2000 Daltons to about 40,000 Daltons.

Additionally, the solid compositions can have the paraffin inhibitor have the structure of Formula 2:

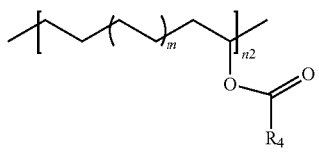

2 wherein $R_4$ is $C_{12}$ to $C_{30}$ alkyl; $R_4$ is $C_{16}$ to $C_{22}$ alkyl; or $R_4$ is $C_{20}$ to $C_{28}$ alkyl.

Further, the solid compositions described herein can have paraffin inhibitor have the structure of Formula 3:

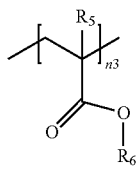

3 wherein $R_5$ is hydrogen, $C_1$-$C_3$ alkyl, phenyl, or benzyl; and $R_6$ is $C_{12}$ to $C_{30}$ alkyl.

When the paraffin inhibitor has the structure of Formula 3, $R_5$ is hydrogen; and $R_6$ is $C_{12}$ to $C_{30}$ alkyl.

When the paraffin inhibitor has the structure of Formula 3, $R_5$ is hydrogen; and $R_6$ is $C_{16}$ to $C_{24}$ alkyl.

When the paraffin inhibitor has the structure of Formula 3, $R_5$ is hydrogen; and $R_6$ is $C_{18}$ to $C_{22}$ alkyl.

When the paraffin inhibitor has the structure of Formula 3, $R_5$ is hydrogen; and $R_6$ is $C_{20}$ to $C_{25}$ alkyl.

When the paraffin inhibitor has the structure of Formula 3, $R_5$ is methyl; and $R_6$ is $C_{12}$ to $C_{30}$ alkyl.

When the paraffin inhibitor has the structure of Formula 3, $R_5$ is methyl; and $R_6$ is $C_{16}$ to $C_{24}$ alkyl.

When the paraffin inhibitor has the structure of Formula 3, $R_5$ is methyl; and $R_6$ is $C_{18}$ to $C_{22}$ alkyl.

When the paraffin inhibitor has the structure of Formula 3, $R_5$ is methyl; and $R_6$ is $C_{20}$ to $C_{28}$ alkyl.

The paraffin inhibitors described herein can be prepared by various methods that would be understood by a person of ordinary still in the art. For example, the polymers of Formulae 1, 2 and 3 could generally be prepared by the synthesis methods disclosed in B. Wei, "Recent advances on mitigating wax problem using polymeric wax crystal modifier," J. Petrol. Explor. Prod. Technol., 2014; D. A. Shipp et al., "Synthesis of Acrylate and Methacrylate Block Copolymers Using Atom Transfer Radical Polymerization," Macromolecules 1998, 31, 8005-8008; and A. Zarrouki et al., "Free Radical Copolymerization of Ethylene with Vinyl Acetate under Mild Conditions," Macromolecules, 2017, 50, 3516-3523, incorporated herein by reference pertaining to synthetic methods disclosed therein.

Additionally, the solid compositions described herein can have the corrosion inhibitor comprise the imidazoline compound of Formula 4.

When the corrosion inhibitor comprises the imidazoline compound of Formula 4, $R_{10}$ is a $C_{10}$ to $C_{20}$ alkyl or a $C_{10}$ to $C_{20}$ alkenyl; or $R_{10}$ is $C_{16}$ to $C_{20}$ alkyl or $C_{16}$ to $C_{20}$ alkenyl.

When the corrosion inhibitor comprises the imidazoline compound of Formula 4, $R_{12}$ and $R_{13}$ are hydrogen.

When the corrosion inhibitor comprises the imidazoline compound of Formula 4, $R_{11}$ is $C_1$ to $C_6$ alkyl substituted with —$N(R_{21})(R_{22})$; $R_{21}$ is hydrogen; $R_{22}$ is —$(CO)R_{23}$; and $R_{23}$ is $C_{10}$ to $C_{20}$ alkyl or $C_{10}$ to $C_{20}$ alkenyl.

Further, the solid composition disclosed herein can have the corrosion inhibitor comprise the imidazoline compound of Formula 5.

When the corrosion inhibitor comprises the imidazoline compound of Formula 5, $R_{10}$ is a $C_{10}$ to $C_{20}$ alkyl or a $C_{10}$ to $C_{20}$ alkenyl; or $R_{10}$ is $C_{16}$ to $C_{20}$ alkyl or $C_{16}$ to $C_{20}$ alkenyl.

When the corrosion inhibitor comprises the imidazoline compound of Formula 5, $R_{12}$ and $R_{13}$ are hydrogen.

When the corrosion inhibitor comprises the imidazoline compound of Formula 5, $R_{11}$ is $C_1$ to $C_6$ alkyl substituted with —$N(R_{21})(R_{22})$; $R_{21}$ is hydrogen; $R_{22}$ is —$(CO)R_{23}$; and $R_{23}$ is $C_{10}$ to $C_{20}$ alkyl or $C_{10}$ to $C_{20}$ alkenyl.

When the corrosion inhibitor comprises the imidazoline compound of Formula 5, $R_{14}$ is $C_1$-$C_6$ alkyl substituted with —$C(O)OR_{24}$; and $R_{24}$ is hydrogen or $C_1$ to $C_3$ alkyl.

A preferred imidazoline corrosion inhibitor composition is commercially available from ChampionX. Additionally, the corrosion inhibitor compositions can be prepared as disclosed in U.S. Patent Application Publication No. 2004/0200996.

The solid compositions described herein can also have the corrosion inhibitor comprise the quaternary ammonium compound having the structure of Formula 6, wherein $R_{25}$ is $C_8$ to $C_{16}$ alkyl.

Preferably, the solid compositions described herein have the paraffin inhibitor comprise the polymer of Formula 1 and the corrosion inhibitor comprise the compound of Formula 4 and the compound of Formula 5, wherein a weight ratio of the paraffin inhibitor to the corrosion inhibitor is from about 1:5 to about 5:1. Preferably, the weight ratio of the paraffin inhibitor to the corrosion inhibitor is from about 1:2 to about 2:1; or the ratio of the paraffin inhibitor to the corrosion inhibitor is about 1:1.

Also disclosed are method for treating a subterranean hydrocarbon-containing reservoir comprising contacting the hydrocarbon with a solid composition described herein.

For the methods of treating a subterranean hydrocarbon-containing reservoir, the solid composition can inhibit or reduce paraffin deposition in the reservoir.

Also, in the methods of treating a subterranean hydrocarbon-containing reservoir, the solid composition can inhibit or reduce corrosion in a piece of equipment in contact with the reservoir.

The amount of solid is based on the water cut of the hydrocarbon fluid, the production rate of the hydrocarbon fluid, the injection capacity and/or solid volume handling, injection frequency, and logistics. For example, for wells producing less than 50 barrels per day with a water cut of greater than 50%, about 10-20 pounds of solids are injected every one to two weeks.

The solid compositions described herein can be administered to a reservoir with various agents simultaneously or close in time. For example, the solid compositions can be administered with an agent selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The agent can comprise an organic solvent. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The agent can comprise a corrosion inhibitor.

The corrosion inhibitor can comprise an imidazoline compound, a quaternary ammonium compound, a pyridinium compound, or a combination thereof.

The corrosion inhibitor can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The corrosion inhibitor can include an imidazoline of Formula (I):

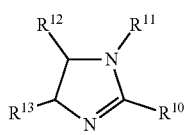

(I)

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$, which is the alkyl mixture typical in tall oil fatty acid (TOFA), and $R^{11}$, $R^{12}$ and $R^{13}$ are each hydrogen.

The corrosion inhibitor can include an imidazolinium compound of Formula (II):

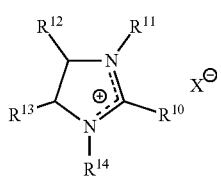

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The corrosion inhibitor can comprise a bis-quaternized compound having the formula (III):

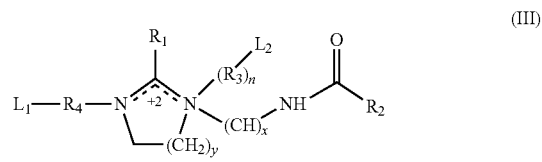

(III)

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{15}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The corrosion inhibitor can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

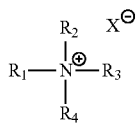

(IV)

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula $[N+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, and $R^{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula $[N+R^{5a}R^{6a}R^{7a}R^{8a}][X^-]$ wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The corrosion inhibitor can comprise a pyridinium salt such as those represented by Formula (V):

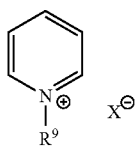

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The corrosion inhibitor can include additional corrosion inhibitors such as phosphate esters, monomeric or oligomeric fatty acids, or alkoxylated amines.

The corrosion inhibitor can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The corrosion inhibitor can comprise an alkoxylated amine. The alkoxylated amine can be an ethoxylated alkyl amine. The alkoxylated amine can be ethoxylated tallow amine.

The agent can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol.

The agent can further include a demulsifier. Preferably, the demulsifier comprises an oxyalkylate polymer, such as a polyalkylene glycol.

The agent can include an asphaltene inhibitor. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The agent can include an additional paraffin inhibitor. Suitable additional paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The agent can include a scale inhibitor. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The agent can include an emulsifier. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The agent can include a water clarifier. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The agent can include a dispersant. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The agent can include an emulsion breaker. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The agent can include a hydrogen sulfide scavenger. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The agent can include a gas hydrate inhibitor. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The agent can include a kinetic hydrate inhibitor. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The agent can include a biocide. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxides, biguanine, formaldehyde releasing preservatives, performic acid, peracetic acid, nitrate, and combinations thereof.

The agent can include a pH modifier. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The agent can include a surfactant. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis (2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

The agent can also include an iron chelator. The iron chelator can be selected from gluconic acid, citric acid, ascorbic acid, tetrakis(hydroxymethyl)phosphonium sulfate (THPS), and combinations thereof.

Compositions used in the methods described herein can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions used in the methods described herein can not contain any of the additional agents or additives.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term alkoxy as used herein or alone or as part of another group is an —OR group, wherein the R group is a substituted or unsubstituted alkyl group as defined herein.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)$_n$, P(O)$_n$, P$R^z$, NH or N$R^z$, wherein $R^z$ is a suitable substituent. Heterocyclic groups include, but are not limited to, 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane. Heterocyclic groups can be unsubstituted or substituted by one or more suitable substituents, preferably 1 to 3 suitable substituents, as defined above.

Having described the disclosure in detail, it will be apparent that modifications and variations are possible without departing from the scope of the invention defined in the appended claims.

EXAMPLES

The following non-limiting examples are provided to further illustrate the present disclosure.

Composition P1 has a 5:1 weight ratio of a polymer of Formula 1 having $R_1$ of $C_{12}$-$C_{14}$ alkyl, and $R_2$ and $R_3$ independently $C_{18}$-$C_{22}$ alkyl to a blend of compounds of Formula 4 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, and $R_{12}$ and $R_{13}$ are hydrogen; and Formula 5 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, $R_{14}$ is alkylene substituted with —C(O))$R_{24}$ where $R_{24}$ is hydrogen, and $R_{12}$ and $R_{13}$ are hydrogen.

Composition P2 has a 1:1 weight ratio of a polymer of Formula 1 having $R_1$ of $C_{12}$-$C_{14}$ alkyl, and $R_2$ and $R_3$ independently $C_{18}$-$C_{22}$ alkyl to a blend of compounds of Formula 4 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, and $R_{12}$ and $R_{13}$ are hydrogen; and Formula 5 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, $R_{14}$ is alkylene substituted with —C(O))$R_{24}$ where $R_{24}$ is hydrogen, and $R_{12}$ and $R_{13}$ are hydrogen.

Composition P9 is a blend of compounds of Formula 4 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, and $R_{12}$ and $R_{13}$ are hydrogen; and Formula 5 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, $R_{14}$ is alkylene substituted with —C(O))$R_{24}$ where $R_{24}$ is hydrogen, and $R_{12}$ and $R_{13}$ are hydrogen.

Composition P10 has a 1:1 ratio of weight ratio of a polymer of Formula 1 having $R_1$ of $C_{20}$-$C_{24}$ alkyl, and $R_2$ and $R_3$ independently $C_{20}$-$C_{28}$ alkyl to a blend of compounds of Formula 4 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, and $R_{12}$ and $R_{13}$ are hydrogen; and Formula 5 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, $R_{14}$ is alkylene substituted with —C(O))$R_{24}$ where $R_{24}$ is hydrogen, and $R_{12}$ and $R_{13}$ are hydrogen.

Composition P11 has a 1:1 weight ratio of a polymer of Formula 1 having $R_1$ of $C_{24}$-$C_{36}$ alkyl, and $R_2$ and $R_3$ independently $C_{20}$-$C_{28}$ alkyl to a blend of compounds of Formula 4 having $R_{10}$ of —$C_{17}H_{33}$ or —$C_{17}H_{35}$, $R_{11}$ of ethylene substituted with —N($R_{21}$)($R_{22}$) where $R_{21}$ is hydrogen and $R_{22}$ is —(CO)$R_{23}$ where $R_{23}$ is —$C_{17}H_{33}$ or —$C_{17}H_{35}$, and $R_{12}$ and $R_{13}$ are hydrogen; and Formula 5 having $R_{10}$ of —$C_{17}H_{33}$ or —$C_{17}H_{35}$, $R_{11}$ of ethylene substituted with —$N(R_{21})(R_{22})$ where $R_{21}$ is hydrogen and $R_{22}$ is —$(CO)R_{23}$ where $R_{23}$ is —$C_{17}H_{33}$ or —$C_{17}H_{35}$, $R_{14}$ is alkylene substituted with —$C(O)R_{24}$ where $R_{24}$ is hydrogen, and $R_{12}$ and $R_{13}$ are hydrogen.

Example 1: Paraffin Inhibition Performance Data

The Dynamic Paraffin Deposition Cell (DPDC) test method was performed as follows: 2 to 3 pellets were placed inside a pouch made out of commercially available 40 μm stainless steel mesh (purchased from McMaster-Carr Product ID 9419T13). The pellet pouches were placed into custom designed DPDC cells containing 60 mL of crude oil (preconditioned at 60° C.) from the Rockies region and 40 mL of synthetic brine (obtained from the representative field water analysis). The brine composition is shown below. The cells were capped off with the deposition probe and cap assembly and placed inside the DPDC shaker bath at 60° C. The pellets were mixed with oil and water for 1 hour at 100 strokes/minute shake rate. At the end of the mixing time the pellet pouches were taken out and the cells were capped off with the same deposition probe and cap assembly. The oil samples treated with the pellets were placed inside the shaker bat at 45° C. and equilibrated for 30 minutes. At the end of equilibration time the deposition probes were connected to chiller lines set at 28° C. The test was run for 18 hours. At the end of the test the individual deposition probes were taken out and paraffin deposit over the deposition probes were quantified. The % inhibition was calculated using the following expression. Where Wuntreated refers to weight of wax deposit for untreated oil and Wtreated refers to weight of wax deposit for treated oil.

% Inhibition=(Wuntreated−Wtreated)/Wuntreated×100

| Salt | Weight, g |
|---|---|
| KCl | 0.05 |
| $CaCl_2$ $2H_2O$ | 0.11 |
| $SrCl_2$ $6H_2O$ | 0.01 |
| $MgCl_2$ $6H_2O$ | 0.09 |
| NaCl | 5.96 |

Brine recipe/800 ml DI water for the performance test studied.

The result for paraffin inhibition performance is tabulated below. The % inhibition for various products are shown in the following bar graph. All of the products show prevention of paraffin deposition compared to blank while two of the products (P1 and P11) show significant paraffin deposition reduction (above 40%).

| Chemical | Pellet Weight Added, g | Deposit weight, g | % Inhibition |
|---|---|---|---|
| Blank | NA | 0.211 | |
| P1 | 1.136 | 0.107 | 49.2891 |
| P2 | 1.274 | 0.169 | 19.905213 |
| P9 | 1.411 | 0.172 | 18.483412 |
| P10 | 1.473 | 0.134 | 36.492891 |
| P11 | 1.258 | 0.091 | 56.872038 |

Example 2: Corrosion Inhibition Performance Data

Corrosion bubble cell tests were performed using the following conditions for compositions described herein. The tests were performed at 80° C., using carbon dioxide saturated fluids with 100% 3% sodium chloride brine (1 L) without hydrocarbon and with continuous carbon dioxide sparge at atmospheric pressure. After about 3 hours of pre-corrosion time (i.e. with no corrosion inhibitor) the various solid paraffin pellets (each having approximately 20% activity) were added to the test cell.

The percent inhibition was determined by comparing the inhibited corrosion rate at about 45 hours after pellet addition and compared with the blank at the same time in the experiment.

The results are given in the table below as well as shown in the graph (black line is the blank, i.e. without added corrosion inhibitor and the various colored lines are different solid paraffin inhibitor options. Three of the solid paraffin inhibitor pellets demonstrated 95% corrosion inhibition or better.

| Chemical | Pellet weight added (g) | Average Baseline before CI addition (mpy) | % Inhibition |
|---|---|---|---|
| Blank | N/A | 435.8 | N/A |
| P1 | 0.550 | 311.7 | 28 |
| P2 | 0.673 | 22.3 | 95 |
| P9 | 0.485 | 12.7 | 97 |
| P10 | 0.479 | 101.7 | 77 |
| P11 | 0.438 | 19.35 | 96 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above methods without departing from the scope of the disclosure, it is intended that all matter contained in the above description shall be interpreted as illustrative and not in a limiting sense.

The invention claimed is:

1. A solid composition comprising a paraffin inhibitor and a corrosion inhibitor, the paraffin inhibitor comprising a polymer having the structure corresponding to Formulae 1, 2, or 3

1

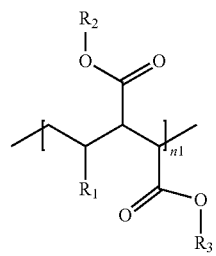

-continued

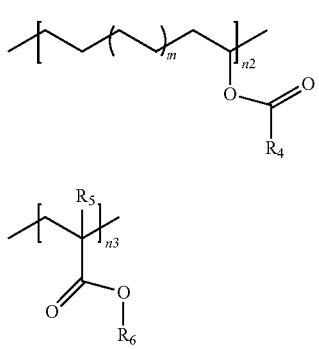

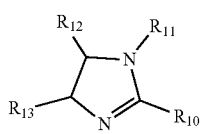

wherein
R$_1$ and R$_5$ are independently hydrogen, alkyl, or alkaryl;
R$_2$ and R$_3$ are independently selected from C$_{10}$ to C$_{30}$ alkyl or C$_{10}$ to C$_{30}$ alkenyl;
R$_4$ and R$_6$ are independently selected from alkyl or alkenyl;
n1 is an integer from 2 to 200;
n2 is an integer from 30-50,000;
n3 is an integer from 50-2000;
m is an integer from 1 to 12; and
the corrosion inhibitor comprising:
(i) an imidazoline compound having the structure of Formula 4:

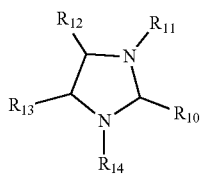

wherein
R$_{10}$ is C$_1$ to C$_{20}$ alkyl or C$_{10}$ to C$_{20}$ alkenyl;
R$_{12}$ and R$_{13}$ are independently hydrogen or C$_1$ to C$_6$ alkyl; and
R$_{11}$ is C$_1$ to C$_6$ alkyl substituted with —N(R$_{21}$)(R$_{22}$) or —C(O)OR$_{24}$,
R$_{21}$ is hydrogen or —(CO)R$_{23}$;
R$_{22}$ is —(CO)R$_{23}$;
R$_{23}$ is C$_{10}$ to C$_{20}$ alkyl or C$_{10}$ to C$_{20}$ alkenyl; and
R$_{24}$ is hydrogen or C$_1$ to C$_6$ alkyl;
or a tautomer thereof;
(ii) an imidazole compound having the structure of Formula 5:

5

R$_{12}$ R$_{11}$
R$_{13}$ N R$_{10}$
N
R$_{14}$ wherein
R$_{10}$ is C$_1$ to C$_{20}$ alkyl or C$_{10}$ to C$_{20}$ alkenyl;
R$_{12}$ and R$_{13}$ are independently hydrogen or C$_1$ to C$_6$ alkyl; and
R$_{11}$ and R$_{14}$ are independently C$_1$-C$_6$ alkyl substituted with —N(R$_{21}$)(R$_{22}$) or —C(O)OR$_{24}$;

R$_{21}$ is hydrogen, —(CO)R$_{23}$, or C$_1$-C$_6$ alkyl substituted with —C(O)OR$_{24}$;
R$_{22}$ is —(CO)R$_{23}$ or C$_1$-C$_6$ alkyl substituted with —C(O)OR$_{24}$;
R$_{23}$ is C$_{10}$ to C$_{20}$ alkyl or C$_{10}$ to C$_{20}$ alkenyl; and
R$_{24}$ is hydrogen or C$_1$ to C$_6$ alkyl;
or a tautomer thereof;
(iii) a quaternary ammonium compound having the structure of Formula 6

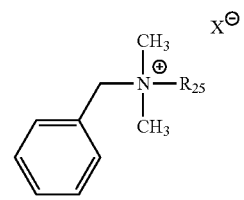

wherein
R$_{25}$ is C$_6$ to C$_{20}$ alkyl or C$_6$ to C$_{20}$ alkyl wherein one or more —CH$_2$— is replaced with —O—; or —(iv) a combination thereof.

2. The solid composition of claim 1, wherein the solid composition is in the form of a pellet.

3. The solid composition of claim 1, wherein the paraffin inhibitor comprises the polymer having the structure of Formula 1.

4. The solid composition of claim 3, wherein R$_1$ is C$_{10}$ to C$_{40}$ alkyl and R$_2$ and R$_3$ are independently C$_{10}$ to C$_{30}$ alkyl.

5. The solid composition of claim 1, wherein the paraffin inhibitor has the structure of Formula 2 and R$_4$ is C$_{12}$ to C$_{30}$ alkyl.

6. The solid composition of claim 1, wherein the paraffin inhibitor has the structure of Formula 3; R$_5$ is hydrogen or methyl; and R$_6$ is C$_{12}$ to C$_{30}$ alkyl.

7. The solid composition of claims 1, wherein the weight average molecular weight of the polymer having the structure of Formula 1 is from about 1000 Daltons to about 100,000 Daltons.

8. The solid composition of claims 1, wherein the corrosion inhibitor comprises the imidazoline compound of Formula 4.

9. The solid composition of claim 8, wherein R$_{10}$ is a C$_{10}$ to C$_{20}$ alkyl or a C$_{10}$ to C$_{20}$ alkenyl.

10. The solid composition of claim 8, wherein R$_{11}$ is C$_1$ to C$_6$ alkyl substituted with —N(R$_{21}$)(R$_{22}$); R$_{21}$ is hydrogen; R$_{22}$ is —(CO)R$_{23}$; and R$_{23}$ is C$_{10}$ to C$_{20}$ alkyl or C$_{10}$ to C$_{20}$ alkenyl.

11. The solid composition of claims 1, wherein the corrosion inhibitor comprises the imidazoline compound of Formula 5.

12. The solid composition of claim 11, wherein R$_{10}$ is a C$_{10}$ to C$_{20}$ alkyl or a C$_{10}$ to C$_{20}$ alkenyl and R$_{12}$ and R$_{13}$ are hydrogen.

13. The solid composition of claims 11, wherein R$_{11}$ is C$_1$ to C$_6$ alkyl substituted with —N(R$_{21}$)(R$_{22}$); R$_{21}$ is hydrogen; R$_{22}$ is —(CO)R$_{23}$; and R$_{23}$ is C$_{10}$ to C$_{20}$ alkyl or C$_{10}$ to C$_{20}$ alkenyl.

14. The solid composition of claim 13, wherein R$_{14}$ is C$_1$-C$_6$ alkyl substituted with —C(O)OR$_{24}$; and R$_{24}$ is hydrogen or C$_1$ to C$_3$ alkyl.

15. The solid composition of claims 1, wherein the corrosion inhibitor comprises the quaternary ammonium compound having the structure of Formula 6, wherein R$_{25}$ is C$_8$ to C$_{16}$ alkyl.

16. The solid composition of claims 1, wherein the paraffin inhibitor comprises the polymer of Formula 1 and the corrosion inhibitor comprises the compound of Formula 4 and the compound of Formula 5, wherein a weight ratio of the paraffin inhibitor to the corrosion inhibitor is from about 1:5 to about 5:1.

17. The solid composition of claim 16, wherein the weight ratio of the paraffin inhibitor to the corrosion inhibitor is from about 1:2 to about 2:1.

18. The solid composition of claim 16, wherein the weight ratio of the paraffin inhibitor to the corrosion inhibitor is about 1:1.

19. The solid composition of claim 1, wherein the weight average molecular weight of the polymer having the structure of Formula 1 is from about 1000 Daltons to about 40,000 Daltons.

20. A method for treating a subterranean hydrocarbon-containing reservoir comprising contacting the hydrocarbon with a solid composition of claim 1.

* * * * *